United States Patent
Kelley, Jr. et al.

(10) Patent No.: US 10,997,715 B2
(45) Date of Patent: May 4, 2021

(54) SYSTEM AND METHOD FOR IMPLEMENTING A MEDICAL IMAGING COMPOSITE AVERAGE AND CLUSTERING TECHNIQUE

(71) Applicant: CEREHEALTH CORPORATION, Littleton, CO (US)

(72) Inventors: John A. Kelley, Jr., Golden, CO (US); Shane Quint, Littleton, CO (US); Lindsay Quandt, Denver, CO (US); Logan Langholz, Menlo Park, CA (US)

(73) Assignee: CereHealth Corporation, Littleton, CO (US)

( * ) Notice: Subject to any disclaimer, the term of this patent is extended or adjusted under 35 U.S.C. 154(b) by 0 days.

(21) Appl. No.: 16/044,612

(22) Filed: Jul. 25, 2018

(65) Prior Publication Data

US 2019/0035077 A1   Jan. 31, 2019

Related U.S. Application Data

(60) Provisional application No. 62/536,532, filed on Jul. 25, 2017.

(51) Int. Cl.
| | |
|---|---|
| *G06T 7/00* | (2017.01) |
| *G06T 7/11* | (2017.01) |
| *G16H 30/20* | (2018.01) |
| *G16H 50/20* | (2018.01) |
| *G16H 30/40* | (2018.01) |
| *G06T 7/136* | (2017.01) |
| *G16H 50/70* | (2018.01) |
| *G16H 10/60* | (2018.01) |

(52) U.S. Cl.
CPC .......... *G06T 7/0012* (2013.01); *G06T 7/0014* (2013.01); *G06T 7/11* (2017.01); *G16H 30/20* (2018.01); *G16H 30/40* (2018.01); *G16H 50/20* (2018.01); *G06T 7/136* (2017.01); *G06T 2207/10108* (2013.01); *G06T 2207/30016* (2013.01); *G16H 10/60* (2018.01); *G16H 50/70* (2018.01)

(58) Field of Classification Search
CPC ....... G06T 7/0012; G06T 7/11; G06T 7/0014; G06T 7/136; G06T 2207/10118; G06T 2207/30016; G06H 30/20; G06H 30/40; G06H 50/20; G06H 50/70; G16H 10/60
USPC .................................................. 382/100, 128
See application file for complete search history.

(56) References Cited

U.S. PATENT DOCUMENTS

| | | | |
|---|---|---|---|
| 10,140,421 B1* | 11/2018 | Bernard | A61B 6/4233 |
| 2016/0180525 A1* | 6/2016 | Reynolds | G06T 7/90 |
| | | | 382/131 |
| 2016/0358312 A1* | 12/2016 | Kolb, V | G06T 5/003 |
| 2017/0000581 A1* | 1/2017 | Tokuda | A61B 90/39 |
| 2017/0084060 A1* | 3/2017 | Bal | G06T 11/008 |

* cited by examiner

*Primary Examiner* — Gabriel I Garcia
(74) *Attorney, Agent, or Firm* — Hunton Andrews Kurth LLP (57) ABSTRACT

A system and method of the present invention are directed to identifying tissue of interest in the body using a large set of heterogeneous medical images acquired over a period of time using consistent acquisition protocols and processing techniques and comparing a single person's medical image to that set at a pixel/voxel level to determine clusters of interest that may be statistically measured and identified for review in the body.

20 Claims, 6 Drawing Sheets

SYSTEM AND METHOD FOR IMPLEMENTING A MEDICAL IMAGING COMPOSITE AVERAGE AND CLUSTERING TECHNIQUE

CROSS REFERENCE TO RELATED APPLICATIONS

This application claims priority to U.S. Provisional Application 62/536,532, filed Jul. 25, 2017, the contents of which are incorporated herein in its entirety.

FIELD OF THE INVENTION

The present invention is directed to the technical field of image analysis. More particularly, the present invention relates to generating a medical imaging composite to identify regions of interest within a medical image.

BACKGROUND OF THE INVENTION

Currently, the identification of regions of interest in a medical image is determined by comparing imaging results to a static set of normal or control groups. In certain instances, the identified control groups are too small of a subset to be statistically significant when measuring regions of interest at a granular level (e.g., pixel or voxel level). Another weakness of a small control group, especially when analyzing subtle differences, is the normal variation contained in the human body in different areas of the body like the brain.

These and other drawbacks exist.

SUMMARY OF THE INVENTION

Accordingly, one aspect of the invention is to address one or more of the drawbacks set forth above. According to an embodiment of the present invention, a medical imaging system comprises: a data store that stores and manages image scans, patient data and composite datasets; a clustering engine that executes a clustering algorithm; and a processor, coupled to the data store and the clustering engine, configured to perform the steps of: selecting a pixel/voxel from a medical image; comparing the pixel/voxel to a composite dataset, wherein the composite dataset is based on a predetermined number of heterogeneous patient image scans; calculating a statistical measurement for the pixel/voxel to quantify a difference from the pixel/voxel and a corresponding pixel in the composite dataset; and applying, via the clustering engine, the clustering algorithm to define one or more regions of interest based on the difference.

According to another embodiment of the present invention, a medical imaging method comprises the steps of: storing and managing, via a data store, image scans, patient data and composite datasets; selecting, via a processor, a pixel/voxel from a medical image; comparing, via the processor, the pixel/voxel to a composite dataset, wherein the composite dataset is based on a predetermined number of heterogeneous patient image scans; calculating, via the processor, a statistical measurement for the pixel to quantify a difference from the pixel/voxel and a corresponding pixel/voxel in the composite dataset; and applying, via a clustering engine, a clustering algorithm to define one or more regions of interest based on the difference.

The system may include a specially programmed computer system comprising one or more computer processors, interactive interfaces, electronic storage devices, and networks.

The computer implemented system, method and medium described herein provide unique advantages to medical providers, patients, clinicians, and other entities in the medical field. Quantitative analysis of brain imaging is currently dependent on comparison to normal control datasets, which are heavily protected and difficult to produce. An embodiment of the present invention provides an innovative imaging system that creates a composite dataset equivalent to that of a normative dataset of control subjects. The innovative system creates the composite dataset or composite average by combining heterogeneous patient scans that have been acquired and analyzed using consistent protocols and processing techniques. Comparison of the composite average to a control dataset reveals the innovative approach to be a viable alternative to control datasets. Combining scans together produces a single image equivalent to the same combination of a much smaller control dataset and therefore is a viable comparison dataset for use in identifying and quantifying regions of interest in various medical imaging scans.

These and other embodiments and advantages of the invention will become apparent from the following detailed description, taken in conjunction with the accompanying drawings, illustrating by way of example the principles of the various exemplary embodiments.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION OF THE INVENTION

The following description is intended to convey an understanding of the present invention by providing specific embodiments and details. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending upon specific design and other needs.

An embodiment of the present invention is directed to system and method for identifying tissue of interest in a body region using a large set of heterogeneous medical images with various conditions and/or potential disorders acquired over a period of time. The larger the number in the composite dataset, the more likely the individual anomalies will be normalized out of each specific area. The set of images may be acquired using a consistent acquisition protocol. The innovative system may compare a single person's medical image to the set of images (or composite dataset) at a pixel/voxel level to determine clusters of tissue that may be statistically measured and identified for review in the body.

An embodiment of the present invention recognizes that this innovative system and technique allows for more granular identification of regions of interest by incorporating analysis of image intensity (grey scale intensity value), SUV (standard uptake value), or other image-derived metrics at a pixel/voxel level. The system may then compare that to an individual image using the same (or similar) registered coordinate in a 2 dimensional or 3 dimensional image using a pixel/voxel's intensity value, SUV, or other image-derived metrics. For example, a z-score may be calculated at a pixel/voxel level for each pixel/voxel within medical image. A z-score may represent a number of standard deviations from the mean a pixel/voxel value is. For example, z-score may represent a measure of how many standard deviations below or above the population mean a pixel/voxel value is. Other calculations and representations may be applied. A clustering algorithm may use a variety of parameters, including but not limited to, minimum size of clusters along with a density of abnormal pixel/voxel within a minimum area to define what constitutes a region of interest.

An embodiment of the present invention is directed to generating and implementing a composite dataset or a composite average that combines images, e.g., 1,000 heterogeneous patient brain scans, that have been acquired and processed using consistent protocols and processing techniques. The system is directed to combining this scan data together to produce an image equivalent to the same combination of a much smaller control dataset. An embodiment of the present invention provides a viable comparison dataset for identifying and quantifying various regions of interest in brain scans as well as scans of other body regions and organs.

Figure 1:
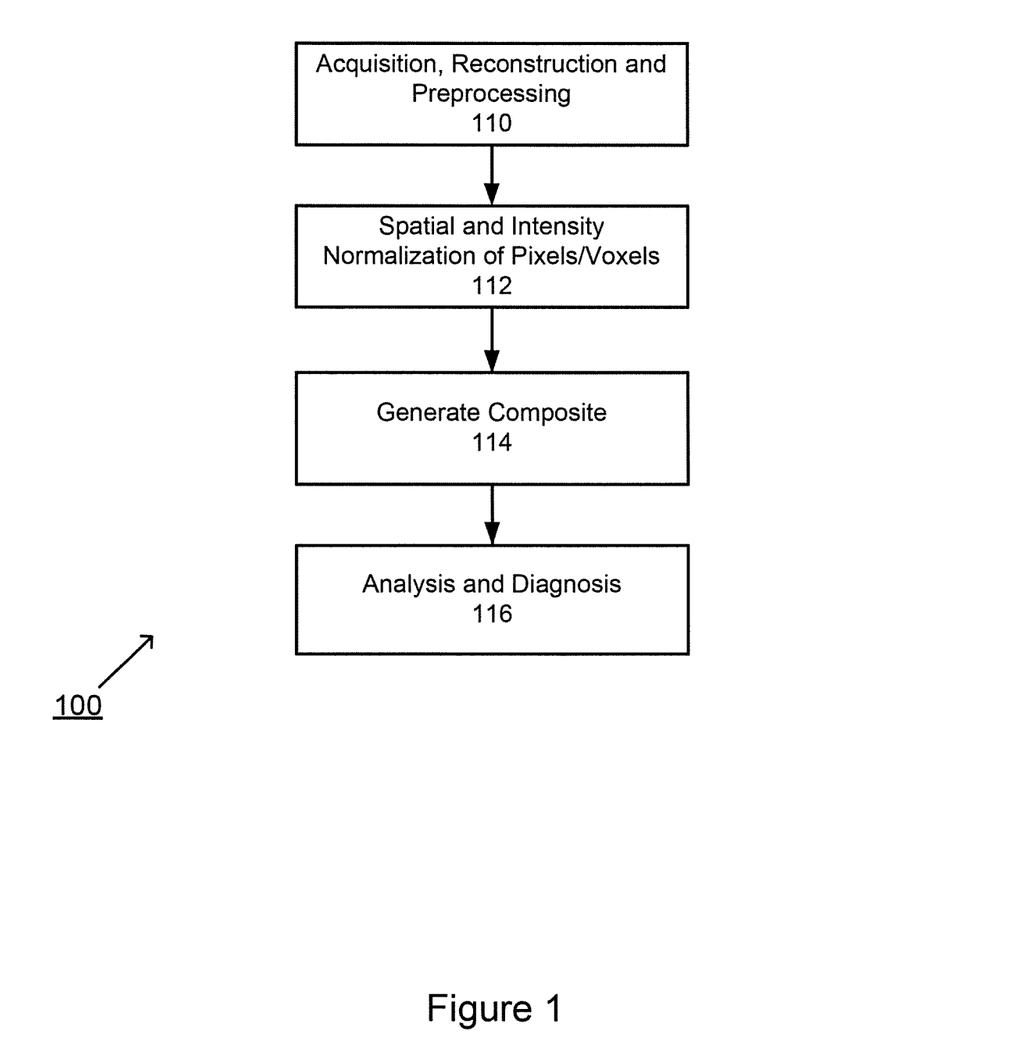
FIG. 1 is an exemplary flow diagram of an imaging composite technique, according to an embodiment of the present invention.

FIG. 1 is an exemplary flow diagram of a composite generation, according to an embodiment of the present invention. At step 110, common acquisition and reconstruction processes may be applied during image collection. For example, the common acquisition and reconstruction processes may include preprocessing, reconstruction, masking and/or other types of filtering and processing. For example, SPECT scans may be reconstructed using filtered back projection and a Butterworth filter. Attenuation correction may also be performed on the images. At step 112, spatial and intensity normalization of each pixel/voxel may be applied. At step 114, the intensity values, SUV, or other image-derived metrics of each pixel/voxel may be combined across all scans in the heterogeneous set of images to generate a single composite image. At step 116, analysis and diagnosis may be provided via an interactive user interface. The order illustrated in FIG. 1 is merely exemplary. While the process of FIG. 1 illustrates certain steps performed in a particular order, it should be understood that the embodiments of the present invention may be practiced by adding one or more steps to the processes, omitting steps within the processes and/or altering the order in which one or more steps are performed. These steps will be described in greater detail below.

At step 110, each image may be acquired, reconstructed, and preprocessed with similar protocols and techniques. An embodiment of the present invention is directed to the use of a large heterogeneous set of medical images acquired in the same (or similar, equivalent or related) protocol throughout a period of time across multiple patient abnormalities and demographics, such as age, gender, etc. A set of acquisition parameters may include tracer, dose, settings, pre-processing, post-processing, conditions, etc. According to an embodiment of the present invention, this acquisition, reconstruction, and preprocessing allows for measurement of a single patient's medical image pixels/voxels to the corresponding pixel/voxels in the plurality of images. Other variations may be realized.

At step 112, each pixel/voxel of an image may undergo spatial normalization by registering the image to another image or to an image template. The set of medical images may be registered to a corresponding anatomical space using a common image template so that each pixel/voxel may be registered to a corresponding location across various images. According to an embodiment of the present invention, this common acquisition and reconstruction process allows for measurement of a single patient's medical image pixels/voxels to a corresponding coordinate location in the plurality of images. The corresponding space or location may represent the same, similar, equivalent and/or related space or location. Other variations may be realized.

At step 112, each pixel/voxel may undergo intensity normalization. Intensity normalization refers to each pixel/voxel being normalized to a predetermined value or set of values. For example, image intensities may be normalized to an average value of an entire region, e.g., the whole brain.

At step 114, the intensity values, SUV, or other image-derived metrics of each pixel/voxel may be combined across all scans in the heterogeneous set of images to generate a single composite image. This may include a calculation of a mean intensity/SUV value for a pixel/voxel or other image-derived metrics in a combined set of images. The calculations may be performed for each pixel/voxel or a set of pixels/voxels.

For example, following spatial and intensity normalization, intensity values, SUV or other image-derived metrics of each pixel/voxel across all (or a subset of) scans may be averaged together to compute a composite average image. In this example, every voxel in the composite may represent an average of 1,000 intensity values at the same location in each scan. Other combination variations may be realized.

At step 116, analysis and diagnosis may be provided via an interactive user interface.

Figure 2:
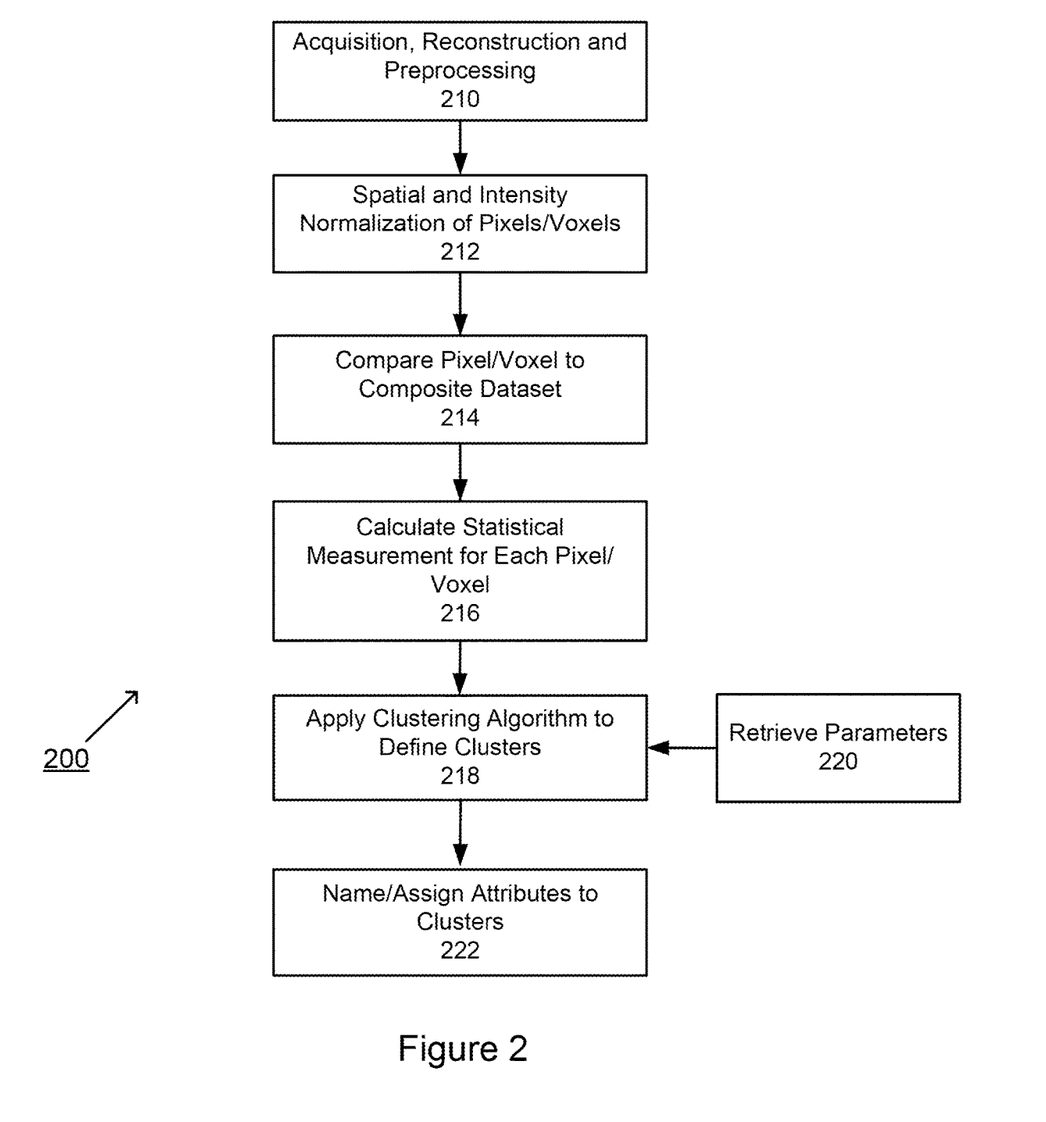
FIG. 2 is an exemplary flow diagram a clustering technique, according to an embodiment of the present invention.

FIG. 2 is an exemplary flow diagram of a clustering technique, according to an embodiment of the present invention. At step 210, common acquisition and reconstruction processes may be applied during image collection. At step 212, spatial and intensity normalization of each pixel/voxel may be applied. At step 214, the pixel/voxel may be compared to a composite dataset. At step 216, statistical measurement for each pixel/voxel may be calculated. At step 218, a clustering algorithm may be applied to define clusters. The clustering algorithm may retrieve parameters at step 220. At step 222, attributes may be assigned to or calculated from the clusters. The order illustrated in FIG. 2 is merely exemplary. While the process of FIG. 2 illustrates certain steps performed in a particular order, it should be understood that the embodiments of the present invention may be practiced by adding one or more steps to the processes, omitting steps within the processes and/or altering the order in which one or more steps are performed. These steps will be described in greater detail below.

At step 210, each image may be acquired, reconstructed, and preprocessed with similar protocols and techniques. An embodiment of the present invention is directed to the use of a large heterogeneous set of medical images acquired in the same (or similar, equivalent or related) protocol throughout a period of time across multiple patient abnormalities and demographics, such as age, gender, etc. A set of acquisition parameters may include tracer, dose, settings, pre-processing, post-processing, conditions, etc. According to an embodiment of the present invention, this acquisition, reconstruction, and preprocessing allows for measurement of a single patient's medical image pixels/voxels to the corresponding pixel/voxels in the plurality of images. Other variations may be realized.

At step 212, each pixel/voxel of an image may undergo spatial normalization by registering the image to another image or to an image template. The set of medical images may be registered to a corresponding anatomical space using a common image template so that each pixel/voxel may be registered to a corresponding location across various images. According to an embodiment of the present invention, this common acquisition and reconstruction process allows for measurement of a single patient's medical image pixels/voxels to a corresponding coordinate location in the plurality of images. The corresponding space or location may represent the same, similar, equivalent and/or related space or location. Other variations may be realized.

At step 214, each pixel/voxel may be compared to its corresponding pixel/voxel in the composite dataset or set of images. An embodiment of the present invention may then compare that pixel/voxel to a large set of clinically acquired images of a heterogeneous group of people over a period of time who followed a similar image acquisition protocol including but not limited to similar tracer dosage, time between injection and scan, and similar camera modalities and settings, etc.

At step 216, statistical measurement for each pixel/voxel may be calculated. This statistical measurement may be derived from intensity values, SUV or other image-derived metric for each pixel/voxel. This value may be used to assign a standard deviation, z-score or other statistical measurement to the same (similar or related) registered location of the pixel/voxel in the individual medical image.

Figure 6:
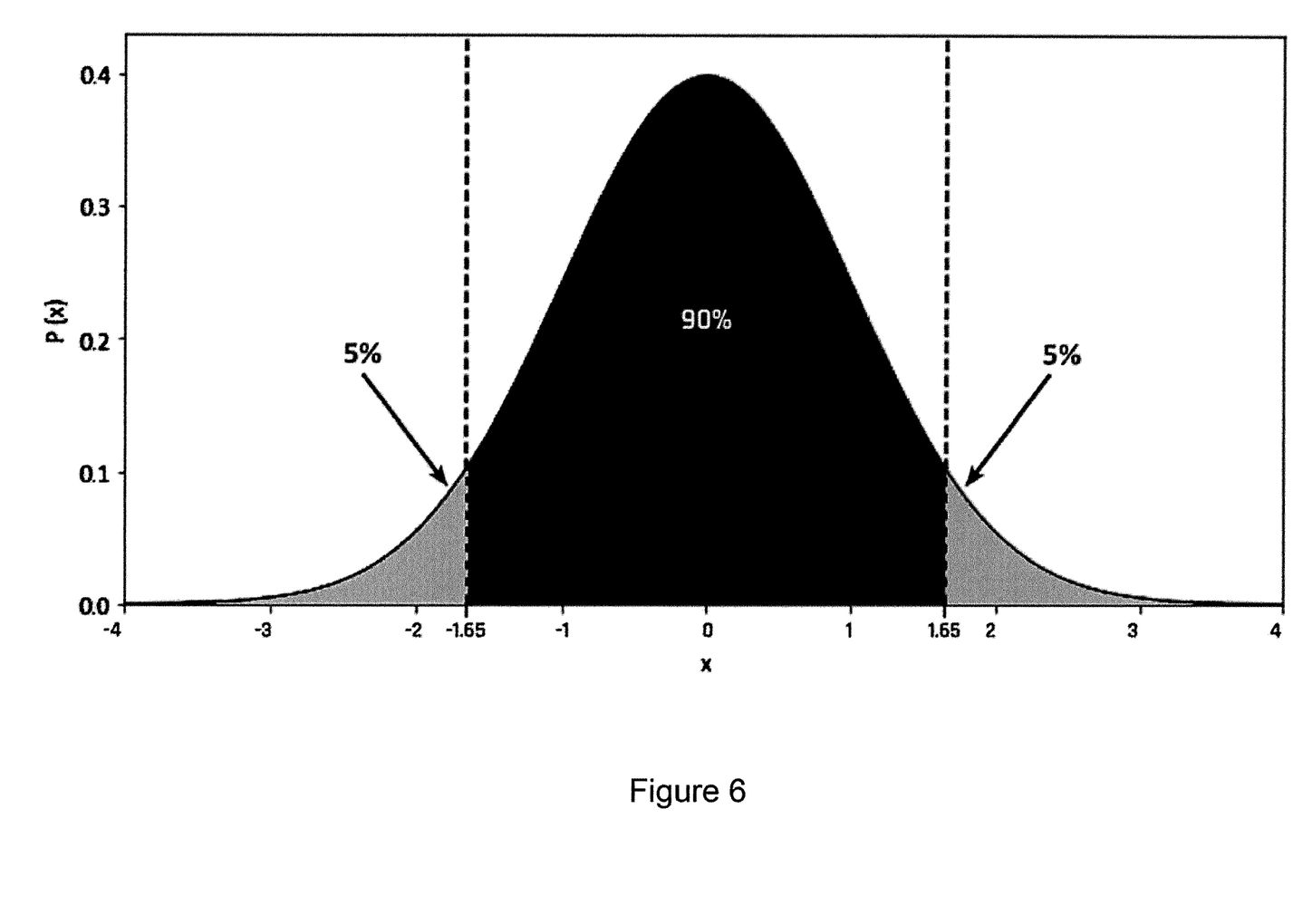
FIG. 6 illustrates an exemplary normal distribution, according to an embodiment of the present invention.

For example, each voxel may be compared to the same voxel in a composite dataset. A z-score may be calculated at every voxel to quantify its difference from the composite and further generate a z-score map. Voxel z-scores may then be aggregated and analyzed according to an anatomical region assignment. Metrics may be derived from each of the standardized regions. For example, ROIs may be exported with various metrics, including but not limited to mean z-score, median z-score, maximum z-score, and minimum z-score. Z-scores may be used to determine parameters for the clustering algorithm. For example, FIG. 6 illustrates an exemplary normal distribution with critical values drawn at ±1.65 x standard deviation (e.g., ±1.65 z-score) where 90% of the curve is contained within these bounds and may constitutes an acceptable range for z-scores. As shown in FIG. 6, P(x) is a representative normal probability density function of random variable "x," such that there is a 90% probability that "x" will have a value between ±1.65 z-score. This threshold for z-scores may be used as a parameter for the clustering algorithm.

At step 218, a clustering algorithm may be applied to define clusters. The clustering algorithm may retrieve parameters at step 220. After all or a subset of pixels/voxels in the individual medical image have an assigned statistical measurement, a clustering algorithm may be applied that defines a cluster of abnormal tissue based on parameters such as the minimum size of cluster and a minimum density of pixels/voxels in the cluster area. Other parameters could be used.

The clustering algorithm may accept or retrieve parameters, such as z-score, cluster size, density of pixels/voxels, etc. This clustering algorithm may define clusters of voxels that have statistical measurement values within predefined thresholds, and make up a cluster greater in size than the minimum cluster size parameter, and have a density of pixels/voxels that are equal to or greater than the density of pixel/voxel parameter.

At step 222, attributes may be assigned to or calculated from the clusters. These clusters may be named and defined attributes may be assigned to or calculated from each named cluster such as what anatomical regions the cluster spans, the mean statistical measurement value of the cluster, and the total volume of the cluster measured in millimeters of volume. Other attributes could be defined and derived.

According to an embodiment of the present invention, the named clusters may be used to assist a medical provider (or other user) in the diagnosis of a medical ailment. Other applications and uses may be realized. Each named cluster in the individual image may represent an area of abnormal tissue as compared to a heterogeneous grouping of medical images using the methods of an embodiment of the present invention. The statistical nature of this approach may remove much of the subjective nature of a radiological medical image interpretation performed by a radiologist.

Figure 3:
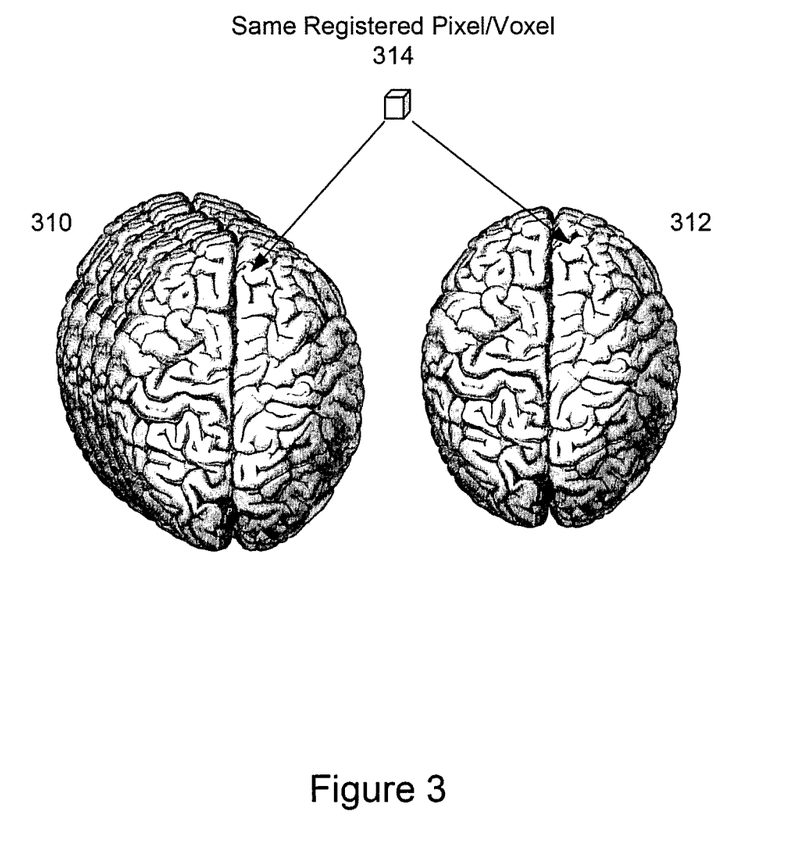
FIG. 3 is an exemplary view of a selected pixel/voxel within a medical image of a human brain, according to an embodiment of the present invention.

The processes of an embodiment of the present invention may be applied to any quantitative medical image that contains intensity values, SUV, or other image-derived metrics at the pixel/voxel level. FIG. 3 is an exemplary view of a selected pixel/voxel within a medical image of a human brain, according to an embodiment of the present invention. Referring now to an embodiment of the present invention in more detail, in FIG. 3 illustrates a top down view of an image representing a medical image of the human brain. The set of images on the left side 310 represent a plurality of heterogeneous medical images acquired over a long period of time with the same acquisition parameters such as tracer, dose, camera settings, etc. The right side image 312 represents a single medical image acquired using the same acquisition parameters such as tracer, dose, camera settings, etc. The three-dimensional box 314 in the center represents a single pixel/voxel to be compared to the same registered location of the pixel/voxel set in the plurality of images 310. The intensity value, SUV, or other image-derived metrics of that same registered pixel/voxel in the single image 312 may be compared to the same registered pixel/voxel location in the plurality of images 310, and a statistical measurement is derived.

In more detail, still referring to the exemplary embodiment of FIG. 3, the statistical measurement calculation of each pixel/voxel in the single medical image 312 may then run through a clustering algorithm that accepts parameters (e.g., z-score, minimum cluster size, density of pixels/voxels).

Figure 4:
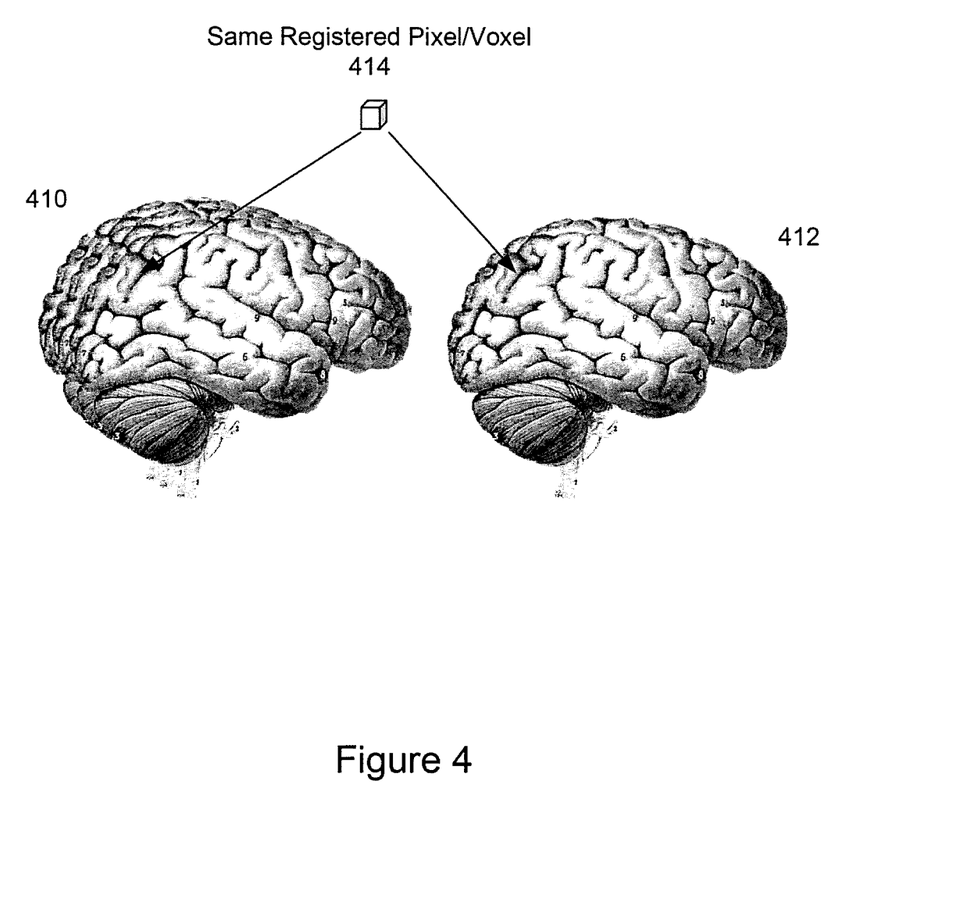
FIG. 4 is an exemplary side view of a selected pixel/voxel within a medical image of a human brain, according to an embodiment of the present invention.

FIG. 4 is an exemplary side view of a selected pixel/voxel within a medical image of a human brain, according to an embodiment of the present invention. Referring now to an embodiment of the present invention illustrated in FIG. 4, there is shown a right side (sagittal) view of an image representing a medical image of the human brain. The set of images on the left side 410 represent a plurality of heterogeneous medical images acquired over a long period of time with the same acquisition parameters such as tracer, dose, camera settings, etc. The right side image 412 represents a single medical image of a single person acquired using the same acquisition parameters such as tracer, dose, camera settings, etc. The three-dimensional box in the center 414 represents the single pixel/voxel to be compared to the same registered location of the pixel/voxel set in the plurality of images 410. The intensity value, SUV or other image-derived metrics of that same registered pixel/voxel in the single image 412 may be compared to the same registered pixel/voxel location in the plurality of images 410, and a statistical measurement value is derived.

In more detail, still referring to the exemplary embodiment of FIG. 4, the statistical measurement calculation of each pixel/voxel in the single medical image 412 may then run through a clustering algorithm that accepts parameters (e.g., statistical measurement, minimum cluster size, density of pixels/voxels). This clustering algorithm may define clusters of pixels/voxels that have statistical measurement values that exceed predefined thresholds, and make up a cluster greater in size than the minimum cluster size parameter, and have a density of pixels/voxels that are greater than the density of pixel/voxel parameter. These clusters may be named and defining attributes may be assigned to or calculated from each named cluster such as what anatomical regions the cluster spans, the mean statistical measurement value of the cluster, and the total area or volume of the cluster.

Figure 5:
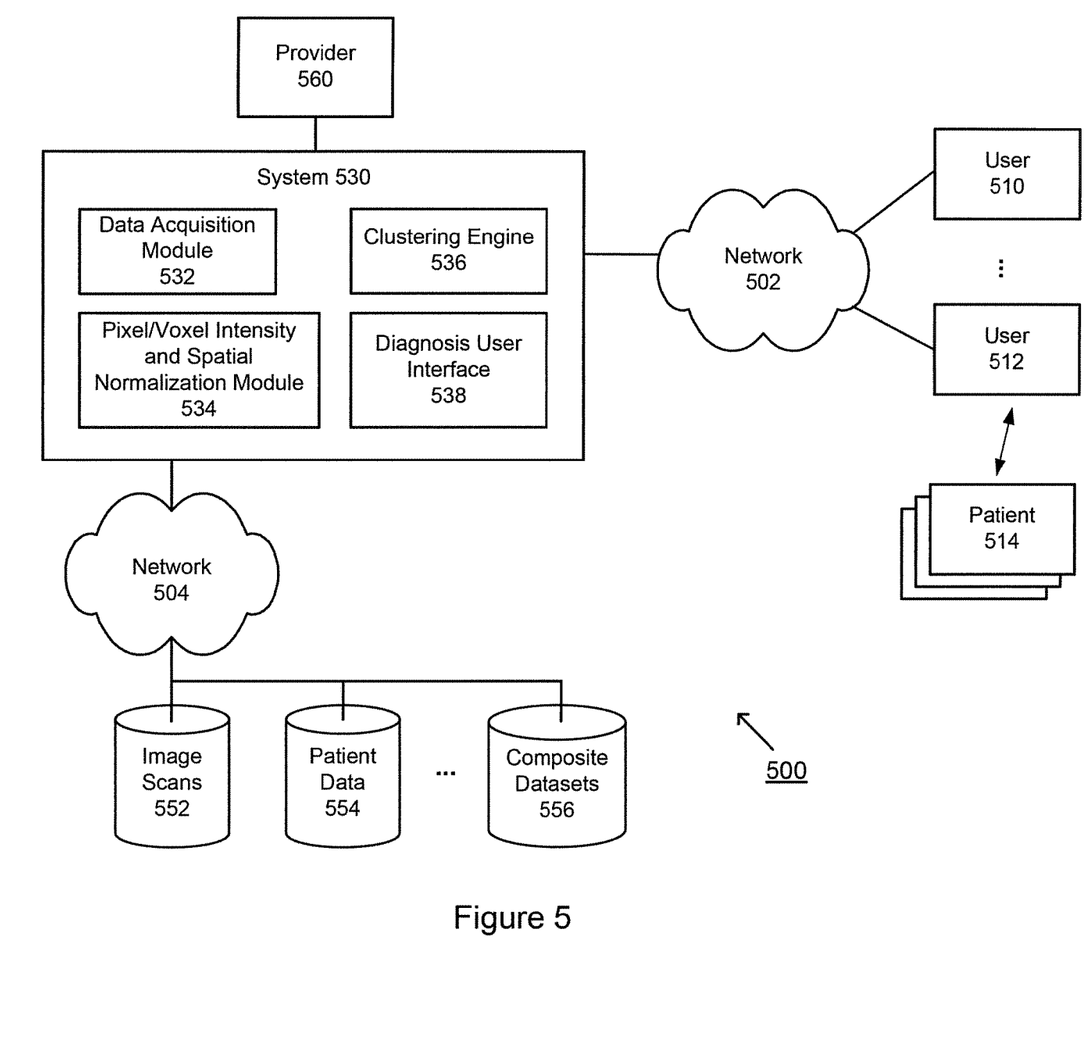
FIG. 5 is an exemplary system diagram of a medical imaging system, according to an embodiment of the present invention.

FIG. 5 is an exemplary system diagram of a medical imaging system, according to an embodiment of the present invention. As illustrated in FIG. 5, Network 502 may be communicatively coupled with one or more data devices including, for example, computing devices associated with end users, represented by User 510, 512 who interact with various patients, represented by 514. Users may represent physicians, technicians, clinicians and/or other users in the medical field. Computing devices may include computers, laptops, workstations, kiosks, terminals, tablets, mobile devices, mobile phones, smart devices, other processor-based devices, etc. Network 502 communicates with System 530 that performs medical imaging analysis. System 530 may include various modules, components and processors, including Data Acquisition Module 532, Pixel/Voxel Registration Module 534, Clustering Engine 536 and Diagnosis User Interface 538. These modules are exemplary and illustrative, System 530 may interact with additional modules, a combination of the modules described and/or less modules than illustrated. While a single illustrative block, module or component is shown, these illustrative blocks, modules or components may be multiplied for various applications or different application environments. In addition, the modules or components may be further combined into a consolidated unit. Other architectures may be realized.

Data Acquisition Module 532 may perform functions, such as filtering data, preprocessing and reconstruction of data. Pixel/Voxel Normalization Module 534 may make calculations and determinations on a pixel/voxel basis. The calculations and determinations may be used to generate a composite dataset. Clustering Engine 536 may comprise a specialized processor that executes a clustering technique or algorithm that identifies clusters and attributes for diagnosis and other analysis. Diagnosis User Interface 538 may receive user inputs and generate results based on the analysis performed by System 530. The results may be provided as interactive graphics and/or other outputs.

System 530 may be communicatively coupled to data storage devices represented by data stores. Specifically, data stores may include Image Scans 552, Patient Data 554 and Composite Datasets 556. Patient Data 554 and may represent data that may be filtered by age, gender, diagnosis and other categories. Patient Data 554 may also include information relating to protocol, preprocessing and post processing. The medical imaging analysis features described herein may be provided by System 530 and/or a third-party provider, represented by Provider 560 which may operate with System 530.

The system 500 of FIG. 5 may be implemented in a variety of ways. Architecture within system 500 may be implemented as hardware components (e.g., module) within one or more network elements. It should also be appreciated that architecture within system 500 may be implemented in computer executable software (e.g., on a tangible, non-transitory computer-readable medium) located within one or more network elements. Module functionality of architecture within system 500 may be located on a single device or distributed across a plurality of devices including one or more centralized servers and one or more mobile units or end user devices. The architecture depicted in system 500 is meant to be exemplary and non-limiting. For example, while connections and relationships between the elements of system 500 is depicted, it should be appreciated that other connections and relationships are possible. The system 500 described below may be used to implement the various methods herein, by way of example. Various elements of the system 500 may be referenced in explaining the exemplary methods described herein.

Network 502, 504 may be a wireless network, a wired network or any combination of wireless network and wired network. Although Network 502, 504 is depicted as one network for simplicity, it should be appreciated that according to one or more embodiments, Network 502, 504 may comprise a plurality of interconnected networks, such as, for example, a service provider network, the Internet, a cellular network, corporate networks, or even home networks, or any of the types of networks. Data may be transmitted and received via Network 502, 504 utilizing a standard networking protocol or a standard telecommunications protocol.

Entity 530 may be communicatively coupled to Data Stores 552, 554, 556 as well as remote storages. These storage components may include any suitable data structure to maintain the information and allow access and retrieval of the information. For example, the storage components may keep the data in an organized fashion. The storage may be local, remote, or a combination. Communications with the storage components may be over a network, such as Network 504, or communications may involve a direct connection between the various storage components and System 530, as depicted in FIG. 5. The storage components may also represent cloud or other network based storage.

The advantages of the present invention include, without limitation, the identification of granular areas of tissue in the human body as compared to a large heterogonous set of medical images that may be statistically measured wherever it exists in the body and each cluster may span multiple anatomical structures. As the number of medical images included in the comparison set increase the accuracy of the identification of abnormal tissue will improve.

An embodiment of the present invention provides a statistical way of identifying regions of interest in the human body using medical imaging as compared to a large heterogeneous grouping of medical images acquired over a long period of time using a consistent acquisition protocol.

Although the embodiments of the present invention have been described herein in the context of a particular implementation in a particular environment for a particular purpose, those skilled in the art will recognize that its usefulness is not limited thereto and that the embodiments of the present invention can be beneficially implemented in other related environments for similar purposes.

As described above, the various embodiments of the present invention support a number of communication devices and components, each of which may include at least one programmed processor and at least one memory or storage device. The memory may store a set of instructions. The instructions may be either permanently or temporarily stored in the memory or memories of the processor. The set of instructions may include various instructions that perform a particular task or tasks, such as those tasks described above. Such a set of instructions for performing a particular task may be characterized as a program, software program, software application, app, or software.

While the foregoing written description of the invention enables one of ordinary skill to make and use various embodiments of the present invention, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A medical imaging system that implements a medical imaging composite, the system comprising:
    a data store that stores and manages image scan data, patient data and a plurality of composite datasets;
    a clustering engine that executes a clustering algorithm; and
    a processor, coupled to the data store and the clustering engine, configured to perform the steps of:
    selecting a pixel/voxel from a medical image;
    comparing the pixel/voxel to a composite dataset, wherein the composite dataset is based on a predetermined number of heterogeneous patient image scans and the composite dataset is from the plurality of composite datasets;
    calculating a statistical measurement for the pixel/voxel to quantify a difference in image-derived metrics associated with the pixel/voxel and a corresponding pixel in the composite dataset; and
    applying, via the clustering engine, the clustering algorithm to define one or more regions of interest based on the difference.

2. The system of claim 1, wherein the predetermined number of heterogeneous patient scans comprise of images obtained and processed using similar acquisition protocols, reconstruction methods, and processing techniques.

3. The system of claim 1, wherein the composite dataset comprises a set of pixels/voxels wherein each pixel/voxel is registered to a specific location of an image scan.

4. The system of claim 1, wherein each pixel/voxel in the composite dataset represents an intensity value, standard uptake value (SUV) or other image-derived metric that is a combination of a predetermined number of intensity values, SUV or other image-derived metrics at the specific location.

5. The system of claim 1, wherein the one or more clusters are further based on predefined parameters.

6. The system of claim 1, wherein one or more attributes are assigned to or calculated from one or more clusters.

7. The system of claim 1, wherein the one or more regions of interest relate to one or more medical image scans.

8. The system of claim 1, wherein the image-derived metrics are represented as intensity values including grey scale intensity values.

9. The system of claim 1, wherein the pixel/voxel is normalized to a predetermined value or set of values.

10. The system of claim 9, wherein the pixel/voxel is spatially normalized by registering the medical image to a corresponding anatomical space using an image template.

11. A medical imaging method that implements a medical imaging composite, the method comprising the steps:
    storing and managing, via a data store, image scan data, patient data and a plurality of composite datasets;
    selecting, via a processor, a pixel/voxel from a medical image;
    comparing, via the processor, the pixel/voxel to a composite dataset, wherein the composite dataset is based on a predetermined number of heterogeneous patient image scans and the composite dataset is from the plurality of composite datasets;
    calculating, via the processor, a statistical measurement for the pixel to quantify a difference in image-derived metrics associated with the pixel/voxel and a corresponding pixel/voxel in the composite dataset; and
    applying, via a clustering engine, a clustering algorithm to define one or more regions of interest based on the difference.

12. The method of claim 11, wherein the predetermined number of heterogeneous patient scans comprise of images obtained and processed using similar acquisition protocols, reconstruction methods, and processing techniques.

13. The method of claim 11, wherein the composite dataset comprises a set of pixels/voxels wherein each pixel/voxel is registered to a specific location of an image scan.

14. The method of claim 11, wherein each pixel/voxel in the composite dataset represents an intensity value, standard uptake value (SUV) or other image-derived metric that is a combination of a predetermined number of intensity values, SUV or other image-derived metrics at the specific location.

15. The method of claim 11, wherein the one or more clusters are further based on predefined parameters.

16. The method of claim 11, wherein one or more attributes are assigned to or calculated from one or more clusters.

17. The method of claim 11, wherein the one or more regions of interest relate to one or more medical image scans.

18. The method of claim 11, wherein the image-derived metrics are represented as intensity values including grey scale intensity values.

19. The method of claim 11, wherein the pixel/voxel is normalized to a predetermined value or set of values.

20. The method of claim 19, wherein the pixel/voxel is spatially normalized by registering the medical image to a corresponding anatomical space using an image template.

* * * * *